United States Patent [19]
Levere et al.

[11] Patent Number: 6,110,472
[45] Date of Patent: Aug. 29, 2000

[54] VITAMIN B12 CONTAINING SCALP AND SKIN TREATMENT COMPOSITIONS

[75] Inventors: Richard D. Levere, Armonk; Nadar G. Abraham; Michal L. Schwartzman, both of Elmsford; Michael W. Dunn, New Rochelle, all of N.Y.

[73] Assignee: Hemogen Inc., Armonk, N.Y.

[21] Appl. No.: 08/285,873

[22] Filed: Aug. 4, 1994

Related U.S. Application Data

[63] Continuation of application No. 07/990,793, Dec. 10, 1992, abandoned.

[51] Int. Cl.$^7$ .............................. A61K 31/70; A61K 7/00
[52] U.S. Cl. ..................... 424/401; 424/70.1; 514/852; 514/52
[58] Field of Search ................... 424/401, 70.1; 514/553, 858, 859, 861, 863, 864, 852, 52

[56] References Cited

U.S. PATENT DOCUMENTS

| | | | |
|---|---|---|---|
| 2,320,479 | 5/1943 | Sperti | 424/553 |
| 2,939,820 | 5/1960 | Gerber | 424/553 |
| 3,876,765 | 4/1975 | Choay | 424/582 |
| 5,053,222 | 10/1991 | Takasu et al. | 424/7 |
| 5,080,908 | 1/1992 | Ono | 514/951 |
| 5,133,958 | 7/1992 | Stuckler | 424/73 |

FOREIGN PATENT DOCUMENTS

| 0170718 | 10/1983 | Japan | 424/553 |
|---|---|---|---|

OTHER PUBLICATIONS

*Remington's Pharmaceutical Sciences*, 17$^{th}$ ed (1985) pp. 1020–1021.
Zviak, *The Science of Hair Care*, p. 89 1986.
Webster's 9$^{th}$ New Collegiate Dictionary p. 324 (1990).

*Primary Examiner*—Thurman K. Page
*Assistant Examiner*—Brian K. Seidleck
*Attorney, Agent, or Firm*—Fulbright & Jaworski, LLP

[57] ABSTRACT

The invention teaches compositions useful for treating conditions characterized by excess exfoliation or hyperkeratinization, such as dandruff. These compositions include vitamin B12 in an amount sufficient to alleviate exfoliation. Dandruff is one condition which may be treated using the formulations.

6 Claims, No Drawings

VITAMIN B12 CONTAINING SCALP AND SKIN TREATMENT COMPOSITIONS

This application is a continuation, of application Ser. No. 07/990,793, filed Dec. 10, 1992, now abandoned.

FIELD OF THE INVENTION

This invention relates to compositions useful in treating skin and scalp disorders. More particularly, it relates to topical formulations useful in treating conditions characterized by excessive exfoliation or hyperkeratinization. Common to all of the formulations of the invention is vitamin B12.

BACKGROUND AND PRIOR ART

A number of human and animal disorders are characterized by excessive cellular exfoliation and/or hyperkeratinization. These conditions include dandruff (Seborrhea sicca), seborrheic dermatitis, acne vulgaris, rosacea, Herpes zoster, psoriasis and eczema, among others. Additional conditions which exhibit excessive exfoliation include various rashes and allergies, including responses to poison oak, ivy and sumac, allergies, chicken pox, insect bites, athlete's foot, actinic keratitis, contact dermatitis, diaper rash, and all forms of pruritis. Various topical formulations are available to alleviate some of the symptoms associated with these conditions.

When the condition is one which affects the scalp, treatment can be carried out via the use of a shampoo. These usually contain a primary detergent, such as a fatty alcohol sulfate, an ether sulfate, a sarconisate or some other anionic material. Additional materials may include aqueous solutions of a soft soap, preservatives, sequestrants, colors, and perfumes. So-called "soapless" shampoos are primarily aqueous solutions of sulfonated oils. Shampoos are used for medicinal purposes because they are easy to formulate and to use, and are generally inexpensive to prepare.

Dandruff, a product of hyperkeratinization, is one condition addressed by special shampoos. These anti-dandruff shampoos or agents generally include ingredients designed to normalize the turnover rate of epidermal cells. Among these ingredients are coal tar, quarternary ammonium compounds, resorcinol, salicylic acid, selenium sulfide, sulfur, undecylenic acid and its derivatives, and zinc pyrithione (i.e., zinc 2-mercaptopyridine N-oxide salt).

An example of the literature on shampoos is U.S. Pat. No. 5,053,222 to Takasu et al., the disclosure of which is incorporated by reference. The patent teaches the various advantages and pitfalls of different anti-dandruff formulations, pointing out that zinc pyrithione, as an antibacterial may; endanger the native ecology of the hair. Formulations of tocopherol esters are stressed, the patent pointing out that many of these are insoluble, do not exhibit long term efficacy, and present difficulty with respect to incorporation in standard formulations.

While many formulations with anti-dandruff efficacy are known, the inventors are unaware of any which incorporate vitamin B12 therein. It has been found, quite surprisingly, that topical formulations which include vitamin B12 therein have an impact on excess exfoliation or hyperkeratinization. In particular, shampoo formulations incorporating vitamins B12 therein have been shown to be effective in alleviating dandruff. This, and other aspects of the invention are set forth in greater detail in the disclosure which follows.

DETAILED DESCRIPTION OF PREFERRED EMBODIMENTS

The invention is a topical formulation useful in the treatment of excessive skin or scalp exfoliation or hyperkeratinization. The formulations are characterized by an amount of vitamin B12 sufficient to alleviate exfoliation or hyperkeratinization, and do not contain any other vitamins or vitamin derivatives. The compositions may include other materials, as described infra, including a pharmacologically acceptable carrier.

In its broadest embodiment, the compositions of the invention may include merely an amount of vitamin B12 sufficient to alleviate exfoliation or hyperkeratinization and a pharmaceutically acceptable carrier. In practice, such formulations are not preferred as much as, e.g., shampoos, hand cremes, skin cremes, salves, balms, and so forth. Particularly preferred are shampoos, including liquids, lotions, gels, emulsions, powders, creme rinses, and other standard formulations of shampoos.

Standard shampoos, in accordance with the invention may include, e.g., the following formulation:

| Ingredient | wt % | Function |
|---|---|---|
| sodium lauryl sulfate (30%) | 40.0 | cleansing agent |
| lauramide DEA | 4.0 | Foam stabilizer |
| disodium EDTA | 0.1 | sequestering agent |
| formaldehyde | 0.04 | preservative |
| FD + C Blue No. 1 | 0.001 | color |
| FD + C Yellow No. 1 | 0.004 | color |
| deionized/distilled water | 55.36 | solvent |

The foregoing is a clear liquid shapoo. An alternative formulation is:

| TEA lauryl sulfate (40%) | 20.0 | cleanser |
|---|---|---|
| Sodium lauryl sulfate (29%) | 20.0 | cleanser |
| cocoamide DEA | 5.0 | Foam stabilizer |
| glycol stearate | 1.0 | opacifying, pearlescent agent |
| disodium EDTA | 0.1 | sequestering agent |
| methylparaben | 0.1 | preservative |
| propylparaben | 0.01 | preservative |
| fragrance | 0.5 | fragrance |
| deionized/distilled water | 53.29 | solvent |

This formulation is a pearlescent or opaque liquid.

Different formulations may be used, and indeed, any of the standard shampoos available over the counter, as well as those available only by prescription, may be used as carriers for the active ingredient, i.e., vitamin B12. When the formulation is to be applied to skin as compared to scalp, any of the standard skin cremes, lotions, gels, liquids, sprays, etc., may be modified to incorporate vitamin B12 therein.

"Vitamin B12", as used herein, refers to all forms of the molecule, as well as to its salts. The fundamental portion of the molecule for purposes of the invention is the coordination compound formed by cobalt and its porphyrin ring. It is to be understood that the vitamin may be treated to render it more soluble in the particular carrier of choice, via, e.g., reacting it to form an acid addition salt, or in any other way which does not impact the fundamental portion of the molecule described supra.

The invention also encompasses therapeutic methods for treating hyperkatinization or excessive exfoliation by administering an amount of vitamin B12 sufficient to alleviate excess exfoliation or hyperkeratinization to the site of the condition. The dose will vary, depending upon the condition, the patent and the severity of the condition, but a general range may be to use a composition containing anywhere from 0.1 to 10.0% by weight of vitamin B12. A particular preferred range runs from about 0.1 weight percent to about 1.0% weight percent, relative to the composition.

The efficacy of the compositions in accordance with this invention is shown in the following example.

EXAMPLE

A standard shampoo ("IVORY"), contains water, ammonium laureth sulfate, ammonium lauryl sulfate, glycol distearate, cocoamide dea, dimethicone, citric acid, sodium hydroxide, fragrance, EDTA, xylene sulfonate, ammonium chloride, methyl chloroisothiazolinone, and methyl isothiazolinone. This "over the counter" composition was modified by including vitamin B12 (1 mg per 100 ml of shampoo, i.e., 1% by weight). The shampoos were provided to subjects having severe dandruff problems. Subjects were shampooed once per day with the formulations, and after 2–4 days, scurf was absent. The shampoos was applied for a period of 10 days, during which time no dandruff was evident.

In a control, the same subjects were then provided with the standard shampoo without vitamin B12, and used this for seven days. Dandruff reappeared. Upon reapplication of the vitamin B12 containing formulations, however, the dandruff was again alleviated.

The foregoing demonstrates the efficacy of the Vitamin B12 containing compositions in accordance with this invention. It will be seen that many skin and scalp directed compositions are known, and incorporation of vitamin B12 therein does not present any difficulties. Thus, the invention as described supra is well within the hands of the skilled artisan, once the key feature, i.e., the use of vitamin B12, is provided.

It will be understood that the specification and examples are illustrative but not limitative of the present invention and that other embodiments within the spirit and scope of the invention will suggest themselves to those skilled in the art.

We claim:

1. Method for treating excessive scalp exfoliation or scalp hyperkeratinization in a subject comprising applying to the scalp of a subject with excessive scalp exfoliation or scalp hyperkeratization an amount of vitamin B12 sufficient to alleviate said excessive scalp exfoliation or scalp hyperkeratization.

2. The method of 1 wherein said exfoliation or hyperkeratization is dandruff.

3. The method of claim 1, wherein said subject is a human.

4. The method of claim 1, wherein said subject is a non-human animal.

5. The method of claim 1, wherein said vitamin B12 is administered at a concentration of from about 0.1% to about 10% by weight.

6. The method of claim 5, wherein said vitamin B12 is administered at a concentration of from about 0.1% to about 1% by weight.

* * * * *